US012387439B2

(12) United States Patent
Knüttel

(10) Patent No.: US 12,387,439 B2
(45) Date of Patent: Aug. 12, 2025

(54) OPTICAL SPECTROSCOPY APPARATUS

(71) Applicant: AKMIRA OPTRONICS GMBH, Potsdam (DE)

(72) Inventor: Alexander Knüttel, Potsdam (DE)

( * ) Notice: Subject to any disclaimer, the term of this patent is extended or adjusted under 35 U.S.C. 154(b) by 228 days.

(21) Appl. No.: 18/189,246

(22) Filed: Mar. 24, 2023

(65) Prior Publication Data

US 2023/0316679 A1    Oct. 5, 2023

(51) Int. Cl.

| A61B 5/00 | (2006.01) |
| A61B 5/11 | (2006.01) |
| A61B 5/22 | (2006.01) |
| G06F 3/01 | (2006.01) |
| G06T 19/00 | (2011.01) |
| G16H 20/30 | (2018.01) |
| G16H 80/00 | (2018.01) |

(52) U.S. Cl.
CPC .......... *G06T 19/006* (2013.01); *A61B 5/1107* (2013.01); *A61B 5/22* (2013.01); *A61B 5/4519* (2013.01); *G06F 3/015* (2013.01); *G16H 20/30* (2018.01); *G16H 80/00* (2018.01)

(58) Field of Classification Search
CPC .................................................... A61B 5/0075
See application file for complete search history.

(56) References Cited

U.S. PATENT DOCUMENTS 7,330,267 B1 *  2/2008  Weitzel ................... G01J 3/453
                                                                356/456
2022/0034791 A1 *  2/2022  Zhang ................ G01N 21/8422

FOREIGN PATENT DOCUMENTS

DE    10121499    11/2002

* cited by examiner

*Primary Examiner* — Rochelle D Turchen
(74) *Attorney, Agent, or Firm* — JMB DAVIS BEN-DAVID

(57) ABSTRACT

The invention relates to an optical Spectroscopy apparatus. The Spectroscopy apparatus comprises a transmissive diffraction element on which object light from an examination object is incident via an input aperture of the spectroscopy apparatus, a first reflection element and a second reflection element arranged downstream of the diffraction element with respect to a defined direction of arrival of the object light, a detection unit which is arranged downstream of the diffraction element with respect to object light reflected by the reflection elements, and an evaluation unit which is coupled to the detection unit, wherein the diffraction element forms a beam splitter element, wherein a first light component of the object light is transmitted by the diffraction element, is reflected at the first reflection element and is diffracted at the diffraction element in a wavelength-dependent manner in the direction of the detection unit, wherein a second light component of the object light is diffracted at the diffraction element in a wavelength-dependent manner in the direction of the second reflection element, is reflected at the latter in the direction of the detection unit and is transmitted from the diffraction element and wherein the wavefronts of the first light component and of the second light component interfere at the detection unit depending on the wavelength of the object light to form a respective interference pattern, on the basis of which at least one wavelength of the object light and preferably a plurality of wavelengths of the object light can be determined by the evaluation unit.

19 Claims, 4 Drawing Sheets

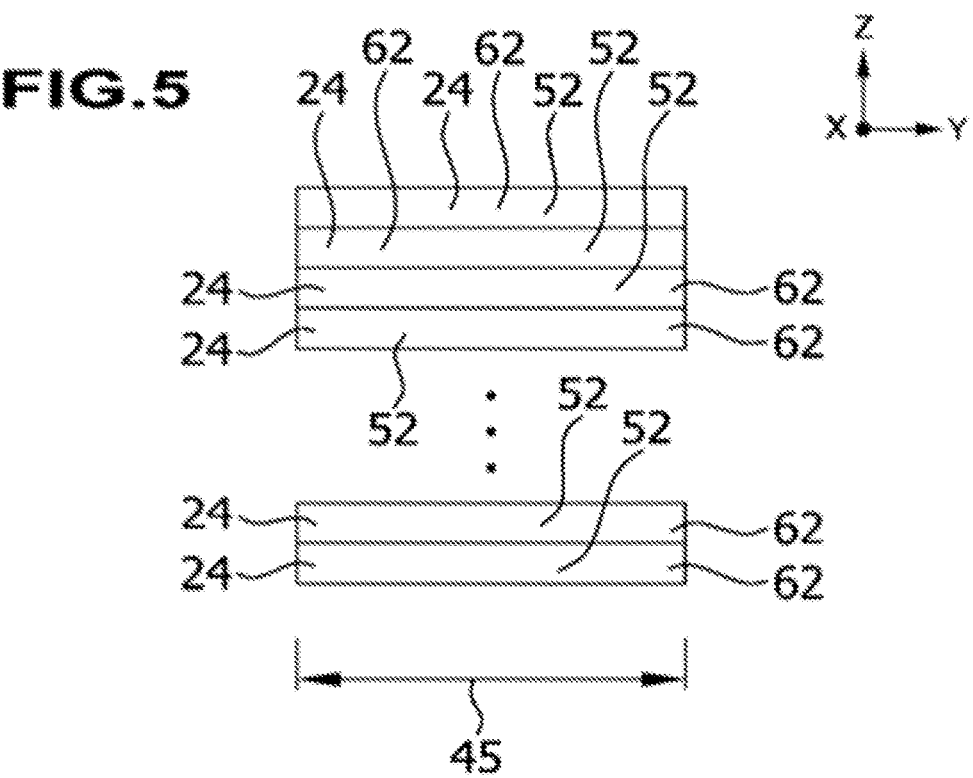
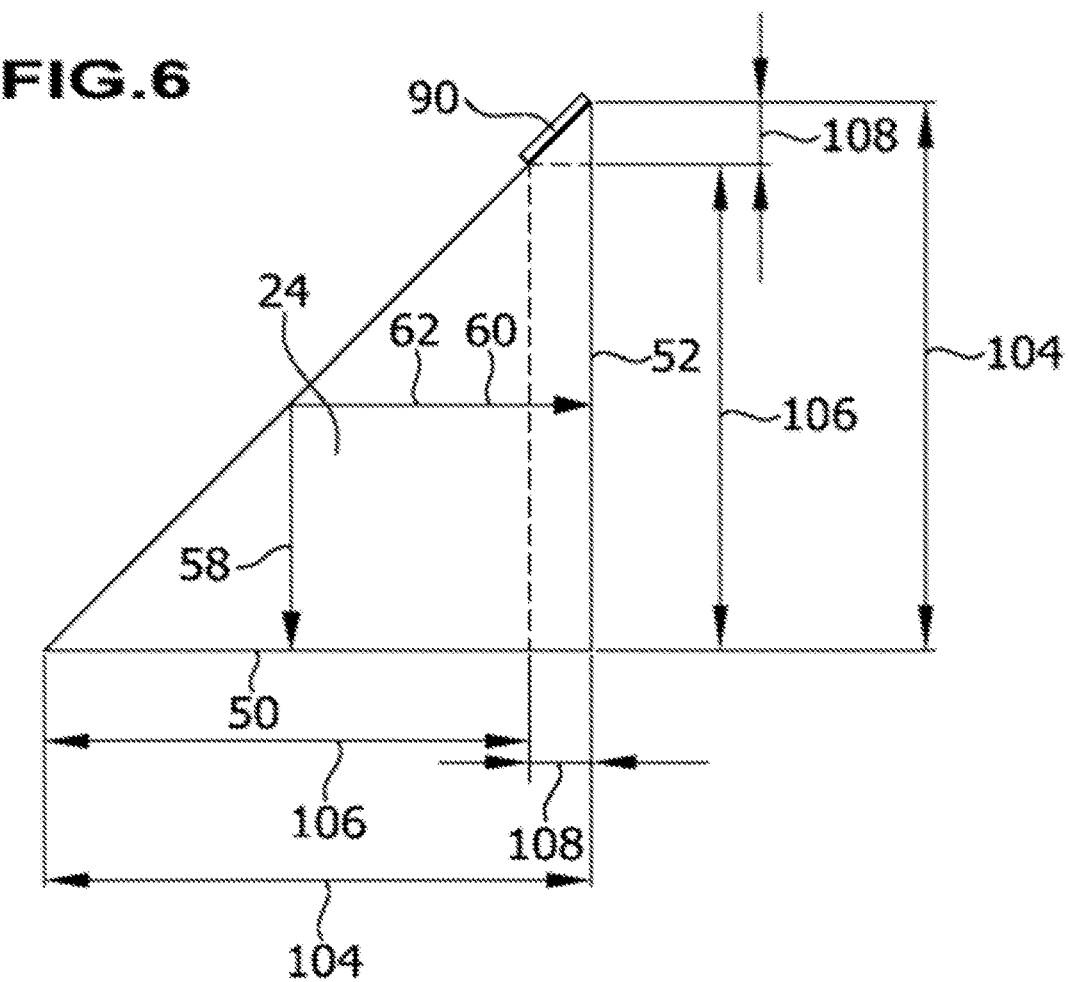

OPTICAL SPECTROSCOPY APPARATUS

FIELD

The present invention relates to an optical spectroscopy apparatus.

BACKGROUND

The present invention relates to an optical spectroscopy apparatus. The optical spectroscopy apparatus comprises or forms a spectrometer for recording spectra in the examination of examination objects. Exemplary applications can be found in examinations with an extended spectral range and delimited large spot or scattering spot. The spectroscopy apparatus can be used, for example, in the regions of absorption spectroscopy, fluorescence spectroscopy as well as particularly Raman spectroscopy.

SUMMARY

The object of the present invention is to provide an optical spectroscopy device with high spectral resolution and a compact design.

This object is solved by an optical spectroscopy apparatus according to the invention, comprising a transmissive diffraction element on which object light emanating from an examination object is incident via an input aperture of the spectroscopy apparatus, a first reflection element and a second reflection element which are arranged downstream of the diffraction element with respect to a defined direction of arrival of the object light, a detection unit which is arranged behind the diffraction element with respect to object light reflected by the reflection elements, and an evaluation unit coupled to the detection unit, wherein the diffraction element forms a beam splitter element, wherein a first light component of the object light is transmitted from the diffraction element is reflected at the first reflection element and diffracted at the diffraction element in the direction of the detection unit in a wavelength-dependent manner, wherein a second light component of the object light is diffracted at the diffraction element in the direction of the second reflection element in a wavelength-dependent manner, is reflected at the second reflection element in the direction of the detection unit, and is transmitted by the diffraction element, and wherein the wavefronts of the first light component and of the second light component interfere at the detection unit depending on the wavelength of the object light to form a respective interference pattern, on the basis of which at least one wavelength of the object light and preferably a plurality of wavelengths of the object light can be determined by the evaluation unit.

In this case, it is preferably provided that the first light component is first transmitted by the diffraction element before reflection at the reflection element, independent of wavelength, and/or that the second light component is transmitted by the diffraction element after reflection, independent of wavelength.

The invention includes the consideration that the object light is divided at the transmissive diffraction element into two light components, one of which preferably passes through the diffraction element non-diffracted and the other light component is diffracted. After reflection at the reflection elements, the reverse is true, wherein the first light component is diffracted at the diffraction element and the second light component traverses the diffraction element preferably non-diffracted. As a result of the double passage—transmission and diffraction of a respective light component—a spectral resolution can be achieved via the spectroscopy apparatus which is twice as large or essentially twice as large as with only single passage through the diffraction element. The combination of the diffraction element with the reflection elements allows at the same time a compact design, in which the reflection elements can preferably be positioned directly next to the diffraction element and preferably optically coupled. For example, a reflection body arranged immediately next to the diffraction element and comprising the reflection elements can be used, as will be discussed below. Compared to a reflecting diffraction element, the structure of the spectroscopy apparatus is considerably more compact and simpler.

The wavefronts of the first and second light components can interfere at the detection unit and form an interference pattern characteristic for the respective wavelength. The interference pattern is, for example, a fringe pattern. The detection unit comprises, for example, an array of detection elements for detecting the interference pattern. For example, the evaluation unit determines the underlying wavelength of the object light by Fourier transforming the interference pattern. By application of the diffraction element, the interference patterns differ due to the respective angle between the wavefronts of the two light components. Thus, it is particularly possible to determine a plurality of wavelengths in the object light.

On the one hand, a high light yield can be achieved via the extended input aperture of the spectroscopy apparatus, through which preferably the entire diffraction element can be illuminated. On the other hand, the spectroscopy apparatus preferably comprises a large acceptance angle at which object light can be incident from the examination object. This enables the investigation of even extended scatter spots in terms of high sensitivity. Particularly in combination with the improved spectral resolution, this results in a high sensitivity of the spectroscopy apparatus according to the invention so that even weak spectra can be detected.

An exemplary application is Raman spectroscopy, preferably using larger scatter spots (here, for example, an extension of considerably more than about 100 μm to 200 μm can be considered, for example about 1 mm to 5 mm).

Due to the dispersion of the diffraction element, it is preferably provided that the wavefronts of the first light component and the second light component enclose an angle between them which is dependent on the wavelength of the object light and is all the greater the greater the deviation of the wavelength from a predetermined wavelength. In the case of self-interference of the object light, the angle between the wavefronts is characteristic for the wavelength and results from the wavelength-dependent diffraction angle at the diffraction element.

The given wavelength is also referred to as the base wavelength ($\lambda_R$) in the following. In the case of Raman spectroscopy, the predetermined wavelength or base wavelength can be, for example, an elastically (Rayleigh) scattered wavelength of the excitation light. Alternatively, the given wavelength or base wavelength can be, for example, a Stokes-shifted line of the Raman spectrum.

The deviation from the specified wavelength is also referred to as offset wavelength $\Delta\lambda$.

It can be provided that the angle between the wavefronts disappears when light of the given wavelength falls on the diffraction element and the Bragg condition is exactly fulfilled. In this case, the self-interference does not result in an interference pattern, but only contributes to a constant signal at the detection unit. For example, such a constant signal from the detection unit can be disregarded in the evaluation.

According to what has been said, in Raman spectroscopy, for example, the predetermined wavelength may be the elastically (Rayleigh) scattered wavelength for which the Bragg condition of the diffraction element is satisfied.

"Predetermined" in the present case can in particular also mean "predeterminable".

In particular, it is provided that the angle between the wavefronts of the first light component and the second light component is twice as large as an angle between the diffraction direction to the first order for the first or second light component at the predetermined wavelength and the diffraction direction to the first order for the wavelength deviating therefrom. Due to the double passage of object light through the diffraction element, the double angle results from the dispersion of the diffraction element in that both the first light component and the second light component are diffracted. In the direction of propagation of the object light, the two light components are diffracted in a direction pointing away from the respective other light component and thus comprise between them the double angle by which each light component is diffracted at the diffraction element with respect to the predetermined wavelength.

In the previous paragraph, the predetermined wavelength is particularly $\lambda_R$ and the deviating wavelength $\lambda_R + \Delta\lambda$ with offset-wavelength $\Delta\lambda$.

The spectroscopy apparatus is preferably free of moving mechanical elements. This favors a compact design and reliable operation of the spectroscopy apparatus.

The diffraction element is preferably a spectral grating configured as a phase grating.

In a preferred embodiment of the invention, the spectral grating is configured as a VPH (Volume Phase Hologram). The application of a VPH has, for example, the advantage that light outside a predetermined spectral range and/or angular range is transmitted undeflected and can be decoupled, for example, from the spectroscopy apparatus. As a result, the VPH allows wavelength selection and angular selection to eliminate unwanted or insignificant spectral regions. Furthermore, via the VPH, there is high efficiency in diffraction to the first order, wherein preferably diffractions to the higher orders are negligible. This ensures a high signal yield at the detection unit.

The diffraction element, in particular the VPH, is preferably configured in such a way that, with respect to a given wavelength, 50% or approximately 50% of the object light is transmitted as a first light component or diffracted as a second light component, respectively. In this way, the diffraction element can act as a beam splitter element for the first light component and the second light component, each with half the intensity. With the object light divided into the first and second light components respectively by half, an interference pattern with high contrast can be generated during self-interference.

The diffraction element is preferably positioned in Littrow arrangement relative to the direction of arrival with respect to a predetermined wavelength at which an angle of incidence of the object light on the diffraction element corresponds to a diffraction angle of the second light component to the first order. For example, incident light is incident on the diffraction element at a Littrow angle of 45°, wherein the direction of diffraction into the first order comprises an angle with the direction of arrival of 90° under a satisfied Bragg condition. The first and second light components may be oriented at an angle of 90° to each other.

The defined direction of arrival is defined, for example, by an optical axis of the spectroscopy apparatus. This is, for example, the optical axis of a converging lens arranged at the entrance aperture. Object light propagating parallel to the optical axis due to a planar or essentially planar wavefront is also incident under the defined direction of arrival.

In the previous description, it was initially assumed that object light falls on the diffraction element along the defined direction of arrival, for example defined by the optical axis or parallel to it.

However, an extended scatter spot on the examination object can cause object light to be incident in a direction of arrival that differs from the defined direction of arrival and forms an angle with it. In this case, the wavefront of the object light incident in the defined direction of arrival includes a corresponding angle with the wavefront of the light incident in the different direction of arrival.

Advantageously, the wavefronts of the first light component and the second light component include an angle between them that is independent of whether the object light is incident in the defined direction of arrival or in a different direction of arrival that is inclined relative to it by an angle. Regardless of the direction of arrival, the same interference pattern is created in this way during self-interference. This gives the possibility to detect signal contributions of even extended scatter spots and to improve the measurement signal. With the preceding large acceptance angle, a high sensitivity of the spectroscopy apparatus is achieved. Light originating from different regions of the scatter spot can contribute equally to the signal.

The nature of the reflection elements is discussed below.

In a preferred embodiment, the first and second reflection elements are two angularly adjacent sides of at least one reflection body. Preferably, the sides are adjacent to each other at an angle of 90°.

The at least one reflective body may be, for example, a solid body.

It may be provided that the at least one reflection body is arranged immediately adjacent to the diffraction element.

Alternatively, it may be provided that the at least one reflection body is arranged adjacent to the diffraction element with the interposition of an optical manipulation element. Such a manipulation element will be further discussed below.

A gapless direct or indirect coupling of the at least one reflective body to the diffraction element is favorable. A refractive index matching may be provided.

In a preferred embodiment of the invention, the at least one reflective body is an inverted prism. For example, the inverting prism may be a roof prism, particularly a 90° roof prism.

Via the inverted prism or roof prism, the first light component and the second light component are preferably reflected in themselves or almost in themselves.

The inverted prism or roof prism can be configured, for example, with an isosceles-rectangular cross-section. In this case, the hypotenuse faces the diffraction element, and the reflection elements are arranged on the cathets.

For example, the reflection body is symmetrically constructed, wherein a respective optical light path for the first or second light component from the diffraction element to the respective reflection element is of equal length.

It may be desirable to keep the path differences between the first light component and the second light component from the diffraction element to the respective reflection element as small as possible, especially if the line width of the object light is large (for example about 1 nm or more).

Both light components can cover an equally long light path from the diffraction element to the respective reflection element and back.

On the other hand, it may be envisaged that light paths of different lengths are deliberately used.

Accordingly, it can be advantageous if the first light component and the second light component travel light paths of different lengths from the diffraction element to the respective reflection element and back. It can be provided here that the light path of the first light component is longer than the light path of the second light component, or vice versa.

For example, in the latter embodiment, the spectroscopy apparatus is configured to successively emit light with two excitation wavelengths different from one another via an illumination unit, wherein, as a result of the light paths of different lengths, a phase difference between the interference patterns occurring in each case can be achieved. The phase difference is preferably 180° (Pi) and causes a shift of the fringes by half a wave.

Advantageously, the evaluation unit is set up to subtract spectra resulting from the interference patterns from each other. This makes it possible, for example, to reduce and ideally eliminate background signal contributions such as fluorescence—in general, particularly incoherent and/or broadband background signal contributions. At the same time, the useful signal can be increased, wherein in the best case even a doubling is conceivable.

The above mode of operation can prove advantageous specifically in the case of Raman spectroscopy. In difference spectroscopy, for example, the difference in excitation wavelengths is in the order of magnitude of the linewidth of the Raman spectrum.

It is advantageous, if the spectroscopy apparatus comprises or forms a plurality of sub-apertures, wherein the object light incident on the diffraction element is split within a respective sub-aperture into a first light component and a second light component and reflected at the respective first or second reflection elements. The smallest possible path length differences between the first light component and the second light component can be achieved via the respective sub-aperture. Within the respective sub-aperture, an interference pattern with high visibility can be generated in this way.

The totality of the sub-apertures corresponds in particular to a detection aperture of the detection unit.

In particular, within each sub-aperture the spectral information about the at least one wavelength of the object light is contained in the wavefronts of the first light component and the second light component originating from this sub-aperture. Accordingly, depending on each sub-aperture, an independent and evaluable interference pattern can be provided. There is an advantage of high signal strength over the entire aperture if it is assumed that the signal originating from a sub-aperture drops off at its edge. Conveniently, the contributions from the individual sub-apertures can be added up to obtain the overall signal.

It is particularly conceivable that spectra for each sub-aperture are determined by the evaluation unit and the spectra are added up.

It is advantageous if a plurality of reflection elements arranged side by side in the direction of extension of the diffraction element are provided, each with a first reflection element and a second reflection element, which reflection elements define a respective sub-aperture. This enables a structurally simple implementation of the sub-apertures.

In advantageous embodiments, for example, approximately 5 to 15 reflection bodies can be provided, which are arranged next to one another in the direction of extension. For example, about 10 reflection bodies may prove advantageous.

In another embodiment, for example, only one reflection body and no sub-aperture is provided.

The respective sides of the reflection bodies are preferably adjacent to each other at an angle of 90° and define the reflection elements.

The reflection bodies may be symmetrically configured with respect to, as mentioned preceding, equally long light paths of the first light component and the second light component.

Alternatively, it can be provided that the reflection bodies are designed asymmetrically with respect to the light paths of the first light component and the second light component of different lengths, as mentioned above.

The reflection bodies are preferably designed as inverted prisms, for example as roof prisms. In particular, the reflection bodies are preferably 90° roof prisms. In practice, a sub-aperture of about 1 mm, for example, may prove advantageous for a compact design of the spectroscopy apparatus.

To define sub-apertures of the same size, the reflection bodies are preferably of the same size and preferably identical in design.

The signal contributions from different sub-apertures can be detected and separated, for example, because the respective illuminated positions at the detection unit are known.

Optionally, it can be provided that the spectroscopy apparatus comprises at least one optical manipulation element assigned to a respective sub-aperture. The manipulation element is, for example, a phase mask or an amplitude mask. The nature of the manipulation element can be used by the evaluation unit during the evaluation. For example, beam shaping can be performed via the manipulation element.

("beamshaping") can be performed via the manipulation element, which facilitates the addition of the signal contributions of the sub-apertures to a signal with higher signal strength and/or high resolution.

Advantageous can be the application of manipulation elements, for example to influence the wavefronts at the edges of the reflection elements, for example to apodize unwanted reflections.

Advantageously, by means of at least one manipulation element on a reflective body, light paths of different lengths, as mentioned preceding, of the first light component and the second light component are achievable.

For example, the manipulation element is designed as an amplitude mask, for example to achieve different path lengths in difference spectroscopy. The amplitude mask can, for example, block or shade a part of the first light component or the second light component within a respective sub-aperture.

Alternatively, or additionally, a phase mask may be provided as a manipulation element, for example.

The at least one manipulation element is arranged, for example, between the diffraction element and the reflection body. Alternatively, or supplementarily, the at least one manipulation element may be arranged, for example, on the first reflection element and/or on the second reflection element.

Preferably, the evaluation unit determines the at least one wavelength of the object light depending on the at least one interference pattern that is due to the at least one sub-aperture. In particular, the at least one wavelength can be determined based on a respective interference pattern.

Instead of a plurality of reflection bodies, as mentioned, it may be provided that only one reflection body is provided, comprising the first reflection element and the second reflection element. In this case, for example, no sub-apertures are provided. The aperture of the one reflection body covers, for example, the entire detection aperture of the detection unit. The one reflection body is, for example, an inverted prism or roof prism.

A substantially planar two-dimensionally extended diffraction element may be provided, wherein the reflection bodies are configured to extend along a spatial direction along the diffraction element and are arranged side by side along the second spatial direction.

The spectroscopy apparatus preferably comprises an illumination unit which comprises at least one preferably monochromatically designed light source for illuminating the examination object.

The light source may in particular be a laser light source.

Excitation light in Raman spectroscopy, for example, may be narrow-band, for example with a linewidth of about 0.1 nm or less.

For example, excitation light may be focused to a point focus or a line focus, preferably resulting in an extended scatter spot, respectively.

"Point focus" and/or "line focus" in the present case does not necessarily mean a geometric point-shaped focus or a geometric line-shaped focus, respectively. In particular, for example, a focus on an extended point or a focus on an extended line may take place. For simplicity, the terms "point focus" and "line focus" are used hereinafter.

Provisions may be made for optionally emitting light of different wavelengths from the at least one light source. For example, light of different wavelengths is emitted in a timed manner, i.e., different wavelengths can be emitted at successive times, for example.

The evaluation unit can be synchronized with the illumination unit in order to relate a spectrum determined in this process to the respective wavelength, depending on the emission of light of different wavelengths.

The spectroscopy apparatus preferably comprises, upstream of the diffraction element with respect to the direction of arrival, a convex lens or concave mirror for collecting object light starting from the examination object. For a point focus, for example, a spherical lens is used. In a line focus, the lens may be a cylindrical lens, for example, wherein a combination with a spherical lens is also possible. Alternatively, for example in the case of individual foci lying side by side in a line, a one-dimensional lens array with spherical lenses may be provided, in particular if the reflective body or bodies is/are extended along a spatial direction as explained preceding. For example, the lenses are microlenses arranged side-by-side. For example, the lenses are aligned along the non-spectral spatial direction parallel to the fringes of the interference pattern, because in this case no excessively steep angles of incidence perpendicular to the fringes can occur.

The spectroscopy apparatus comprises upstream of the diffraction element with respect to the direction of arrival, for example, at least one blocking element for filtering or reflecting object light outside a predetermined spectral range. For example, a VPH capable of suppressing several orders of magnitude of the unwanted spectral range is used as the blocking element. In a Raman spectroscopy application, preferably several orders of magnitude of the exciting Rayleigh light can be suppressed.

Preferably, object light outside a predetermined spectral range is transmitted by the diffraction element. For such object light, the diffraction element, for example the VPH, can act as a transparent optical element to couple out unwanted or insignificant spectral regions.

Object light outside a predetermined spectral range can preferably be coupled out via the first reflection element and/or via the second reflection element.

For this purpose, the reflection elements can be dichroic reflection elements, for example.

If reverse prisms are used as explained above, counter prisms can be coupled to them, for example, to enable unwanted light to be decoupled. Preferably, the counter prisms are optically coupled to the reversing prisms while adapting the refractive index.

It can be advantageous for the decoupling of light of undesired spectral ranges if a counter body to the at least one reflection body is arranged on the incidence side of the diffraction element, in particular a counter prism if at least one reversing prism is used. In the case of a plurality of reflection bodies, for example, only one counter body can be provided, the aperture of which matches the incidence-side apertures of the reflection bodies. The counter body and the at least one reflection body may then together take the form of a beam splitter cube, for example, wherein the diffraction element forms the "beam splitter layer".

The detection unit preferably comprises a matrix detector or a line detector. All possible light-sensitive detection units are conceivable (CCD detector or similar).

A sampling rate may be, for example, about 100 to 1000 frames per second, depending on the application, wherein lower or higher sampling rates are also conceivable.

BRIEF DESCRIPTION OF THE DRAWINGS

The following description of preferred embodiments of the invention, in conjunction with the figure, serves to explain the invention in more detail. Showing:

FIG. 5: a schematic representation of reflection bodies of the spectroscopy apparatus of FIG. 1 in the direction of view of arrow "5" in FIG. 1; and FIG. 6: a schematic representation of a reflection body of the spectroscopy apparatus according to the invention, configured as a roof prism, wherein the incident side of a reflection element is partially shaded.

DETAILED DESCRIPTION

Figure 1:
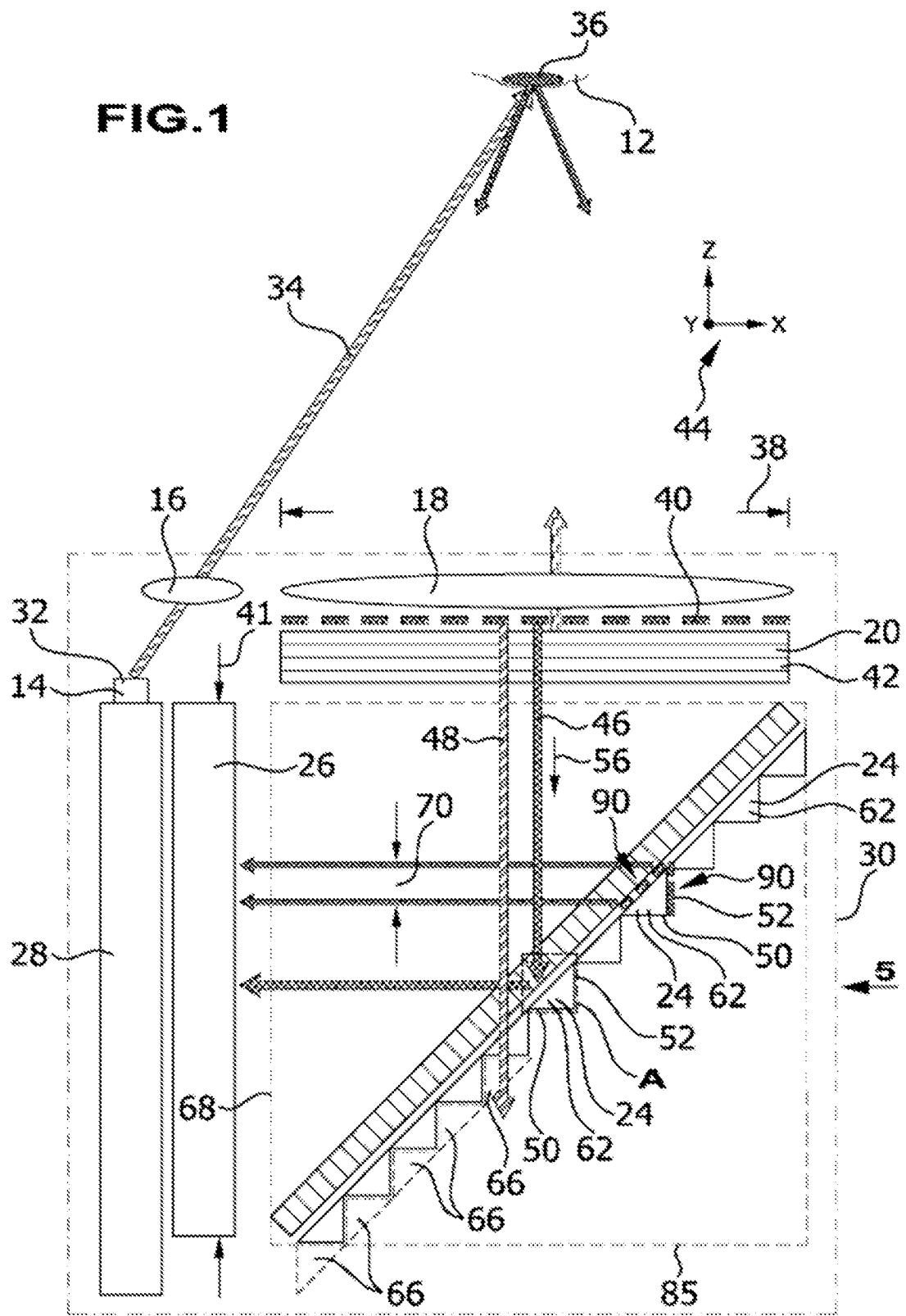
FIG. 1: a first preferred embodiment of the spectroscopy apparatus according to the invention in schematic representation.
Figure 2:
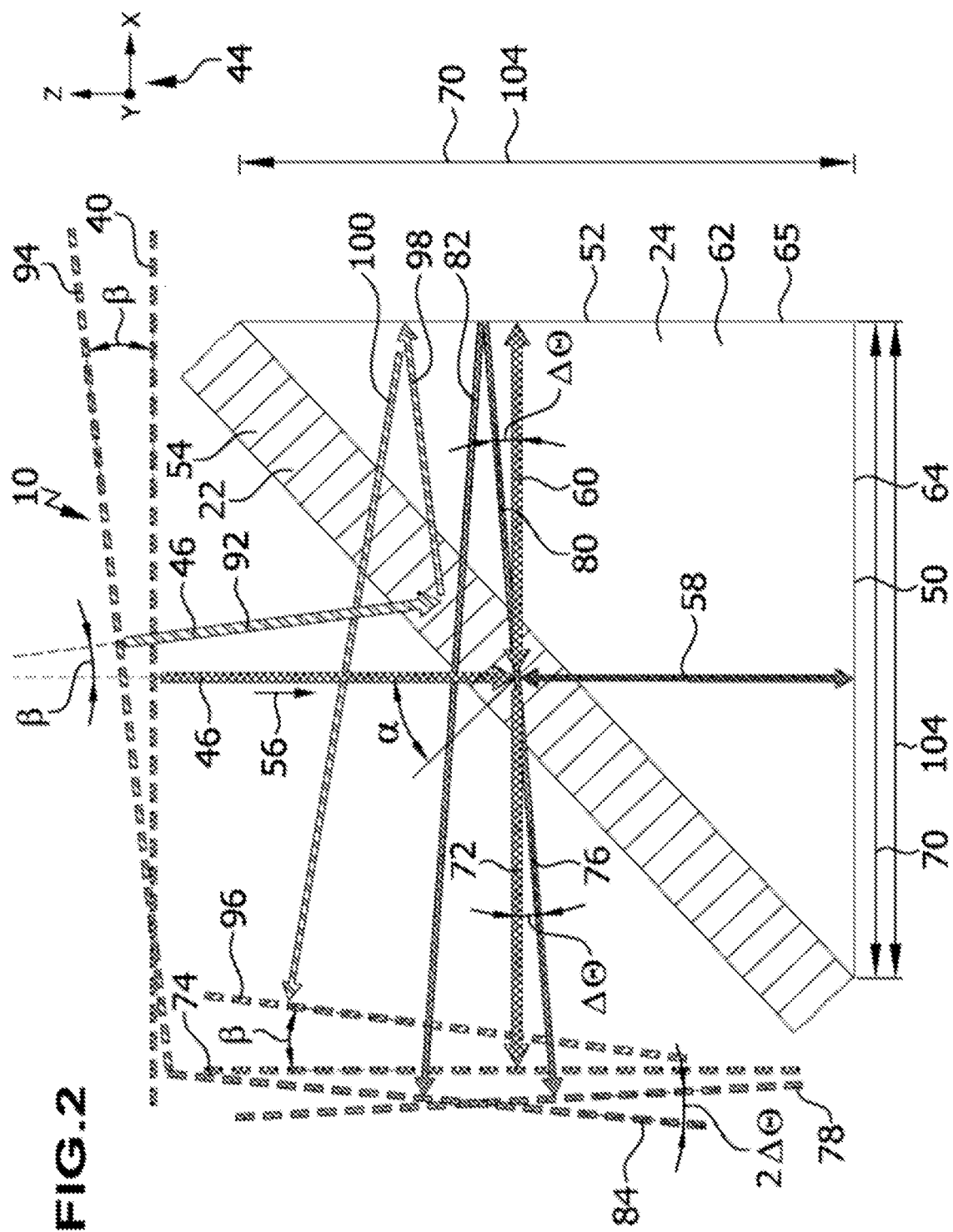
FIG. 2: an enlarged schematic representation of the spectroscopy apparatus in FIG. 1, for example according to detail A.

A preferred embodiment of the spectroscopy apparatus according to the invention is shown schematically in FIG. 1 and partially in FIG. 2 and is assigned the reference sign 10 therein, respectively. The spectroscopy apparatus 10 comprises or forms in particular a spectrometer.

FIG. 1 shows an application of the spectroscopy apparatus 10 for the examination of an examination object 12, which may be, for example, a human body or an animal body. However, the application of the invention is not limited to the field of medical technology, but also to the examination of inanimate subjects, although the compact design of the spectroscopy apparatus 10 makes it particularly suitable for this field. For example, the spectroscopy apparatus 10 can also be used in body cavities. In the application illustrated in FIG. 1, the spectroscopy apparatus 10 is used, for example, for diabetes diagnostics.

The spectroscopy apparatus 10 comprises an illumination unit 14, a focusing lens 16, a converging lens 18, a blocking element 20, a transmissive diffraction element 22, at least one reflection body 24, a detection unit 26 and an evaluation unit 28. Here, in particular the lenses 16, 18 and the blocking element 20 are optional.

The spectroscopy apparatus 10 may comprise a housing 30, schematically indicated in FIG. 1, in which its components are arranged. It may be envisaged that individual ones of the preceding components are arranged outside the housing 30.

For example, the evaluation unit 28 is arranged outside the housing 30. The evaluation unit 28 is coupled to the detection unit 26 and preferably to the illumination unit 14, and may be wired and/or wirelessly coupled thereto.

The application of the spectroscopy apparatus 10 is explained below using the example of a Raman spectrum starting from the examination object 12, but is not limited thereto.

In the exemplary application, a light source 32 of the illumination unit 14 emits excitation light 34. The light source 32 is, for example, a laser light source, wherein the excitation light 34 is monochromatic and preferably as narrow-band as possible. In the case of Raman spectroscopy, for example, the linewidth is less than about 0.1 nm. The wavelength may be in the region of the visible spectrum or in the IR region.

In the figure, the textured arrows indicate light of different wavelengths (color), wherein the respective wavefronts of the respective light are textured with the respective texture.

The excitation light 34 is focused on the examination object 12 via the convex lens 18 and excites the tissue in the region of a focus. Excitation takes place via a spread-out scatter spot 36. In the present application, a diameter of the scatter spot 36 is typically much greater than about 100 μm, for example, 1 mm to 2 mm.

The focus may be a point focus or a line focus. Accordingly, the convex lens 18 may be a spherically curved lens or a cylindrical lens. In the latter case, a one-dimensional lens array with spherical lenses may alternatively be used. The lenses are, for example, microlenses arranged side by side perpendicular to the drawing plane in the present example. In a respective manner, the cylindrical lens may be extended perpendicular to the drawing plane.

A line focus or a plurality of foci juxtaposed in a line, for example perpendicular to the drawing plane, especially in conjunction with microlenses, allows the spectroscopy apparatus 10 to have a low build height, relative to the direction of arrival of the object light. Such a configuration is advantageous, for example, for the application in devices with a flat design, for example smartphones or tablet computers.

In the present application example, the excitation light 34 comprises the wavelength $\lambda_R$. In the examination object 12, elastic Rayleigh scattering takes place with $\lambda_R$ and inelastic Stokes-shifted Raman scattering with wavelength $\lambda_S = \lambda_R + \Delta\lambda$ wherein $\Delta\lambda$ is referred to as the offset wavelength.

The scattered light is collected via the convex lens 18, which in this case defines an input aperture 38 of the spectroscopy apparatus 10, and subsequently propagates with essentially planar wavefront 40. In the present example, the size of the input aperture of the convex lens 18 matches the size of a detection aperture 41 of the detection unit 26.

Downstream of the convex lens 18, the blocking element 20 is arranged. The blocking element 20 is, for example, a filter element which may be implemented as a preferably narrow-band VPH 42. This offers, for example, the possibility of suppressing light with Rayleigh wavelength $\lambda_R$ preferably by several orders of magnitude.

As will be explained in detail below with reference in particular to FIG. 2, Raman radiation impinges on the diffraction element 22 and is deflected towards the detection unit 26 as a result of its properties and the at least one reflection body 24 after passing through twice.

The detection unit 26 comprises an array detector having pixels arranged in a matrix. The interference pattern resulting from self-interference of the wavefronts is picked up by the detection unit 26. Information relating to this is transmitted to the evaluation unit 28. By means of the evaluation unit 28, the respective wavelength of the scattered Raman radiation can be determined.

In the drawing, the respective spectroscopy apparatus is shown only schematically in two dimensions. It is understood that a three-dimensional shape is preferably provided. This is symbolized via the coordinate system 44 in FIGS. 1, 2 and 5. An exemplary arrangement of microlenses perpendicular to the drawing plane has already been discussed.

Accordingly, the respective spectroscopy apparatus 10 can also extend perpendicular to the drawing plane in the Y-direction. In this case, the reflection bodies 24 extend, for example, along the Y-direction (in FIGS. 1 and 2 perpendicular to the drawing plane, in FIG. 5 in the drawing plane). The reference sign 45 indicates the extension of the reflection bodies 24 in the Y-direction.

The Raman light used for the purpose of the measurement is also referred to below as object light 46.

The object light 46 reaches the diffraction element 22 via the VPH 42, which is used to block light outside the desired spectral range. Any other spectral ranges (arrow 48) passing through the VPH 42, which are undesired or insignificant, are transmitted by the diffraction element 22 and can preferably be coupled out via the at least one reflection body 24. For this purpose, for example, a first reflection element 50 or a second reflection element 52 may be configured as a respective dichroic mirror that reflects only object light 46.

The diffraction element 22 is a spectral grating, in particular a phase grating. Preferably, the diffraction element 22 is configured as a VPH 54. For example, the VPH 54 transmits a wavelength window of approximately 50 nm to 100 nm, which is desirable for Raman spectroscopy. For deviating spectral regions (arrow 48), the VPH 54 acts as a transparent window.

For purposes of illustrating the invention, the VPH 54 is shown in the drawing to be too thick relative to the reflective bodies 24. For example, the thickness of the VPH 54 is about 20 μm to 50 μm, with an exemplary edge length of the reflective bodies of about 1 mm.

In the present case, the VPH 54 is positioned in a Littrow arrangement. The corresponding Littrow angle α with respect to a direction of arrival 56 from the focus of the scatter spot 36 is 45° in the present case. The direction of arrival 56 is defined, for example, by an optical axis of the converging lens 18. For object light 46 that is incident parallel to the optical axis, the Littrow condition applies.

The VPH 54 is designed in such a way that approximately 50% of the incident object light 46 is transmitted and approximately the remaining 50% is diffracted into the first diffraction order. In this way, the VPH 54 acts as a beam splitter element for the object light 46.

Hereinafter, the term "light beams" will also be used, although the wave nature of the object light 46 is essential to the operation of the spectroscopy apparatus 10. The use of the term "beam" is merely for ease of description of the invention in the context of the drawing.

Object light 46 with wavelength $\lambda_R$, for which the Bragg condition of VPH 54 is fulfilled and is incident in the direction of arrival 56, is initially transmitted with a first light component (beam 58). A second light component (beam 60) is diffracted to the first order. The angle between the light components 58, 60 is 90°. The VPH 54 forms a beam splitter element.

A plurality of reflective bodies 24 are provided. The reflection bodies 24 are configured as inverted prisms and particularly roof prisms 62, for example made of glass.

In the example of FIGS. 1 and 2, the roof prisms 62 are isosceles 90° prisms in which two sides 64, 65, in this case the cathets, adjoin at an angle of 90°. The hypotenuse faces the VPH 54.

The first reflection element 50 and the second reflection element 52 are formed on the sides 64, 65, respectively. The reflection elements 50, 52 are wavelength sensitive and reflect the incident object light 46. Here, the first reflection element 50 reflects the beam 58 and the second reflection element 52 reflects the beam 60, wherein the reflection of the beams 58, 60 takes place according to the reflection law. If the Bragg condition applies to the object light 46, the beams 58, 60 are reflected into themselves, respectively.

FIG. 1 shows on the left, by way of example and schematically, counter-prisms 66 to the roof prisms 62. The counter-prisms 66, only a part of which is shown dashed for clarity, are optically coupled to the roof prisms with adjustment of the refractive index so that undesired spectral ranges (arrow 48) can be decoupled.

Further, FIG. 1 shows with a dashed line 68 an exemplary counter body arranged on the incidence side of the diffraction element 22 to the at least one reflection body 24. The counter body can be, for example, an inverted prism designed as a roof prism.

The first light component on the outward path and the second light component on the return path are transmitted from the VPH 54, in particular independently of wavelength.

The reflection bodies 24 are identical and arranged in a row along the VPH 54 (FIG. 1).

A respective reflection body 24 defines a sub-aperture 70 within the detection aperture 41 of the spectroscopy apparatus 10 (FIGS. 1 and 2). The sub-apertures 70 of the individual reflective bodies 24 together correspond to the detection aperture 41 (FIG. 1).

In the present case, the sub-aperture 70 comprises a width which respectively corresponds to the extension of the side 65. Due to the symmetrical structure of the reflection bodies 24, this width corresponds respectively to the extension of the side 64 (FIG. 2). On the incidence side, the aperture of each reflective body 24 therefore matches the sub-aperture 70 on the outgoing side of the reflective body. The entirety of the incident apertures matches the input aperture 38.

In further propagation of the object light 46, for which the Bragg condition applies, the first light component 58 is diffracted into the first order via the VPH 54 (beam 72). The second light component 60 traverses the VPH 54 and coincides in the direction of propagation with the first light component according to the beam 72. The reference character 74 identifies the respective two-sided wavefront. Although the wavefronts 74 may interfere, they contribute only to a constant signal in the evaluation unit 28, which can be disregarded in the evaluation.

The situation is different for a different wavelength in the object light 46 in the Raman spectrum, for example a Stokes-shifted wavelength. Let the wavelength be $\lambda_S = \lambda_R + \Delta\lambda$, as explained below. Here, $\Delta\lambda$ is the offset wavelength with respect to the base or Rayleigh wavelength $\lambda_R$.

The object light 46 is again split into a first light component and a second light component at VPH 54, which forms the beam splitter element.

The first light component traverses the VPH 54 along the beam 58, is reflected at the first reflection element 50, and is subsequently diffracted at the VPH 54 to the first order according to the beam 76. The reference character 78 indicates the wavefront of the first light component in this respect. On its way to the reflection element 50, the first light component is accordingly transmitted by the VPH 54 and diffracted at the VPH 54 on its way back from the reflection element 50.

The reverse is true for the second light component. The second light component is first diffracted by the VPH 54 to the first order (beam 80) and then reflected at the second reflection element 52, in the direction of the beam 82. The reference sign 84 identifies the relevant wavefront 84 of the second light component. On the outward path, the second light component is accordingly diffracted by the VPH 54 in the direction of the reflection element 52 and on the return path from the reflection element 52 is transmitted by the VPH 54.

With respect to the base wavelength $\lambda_R$, which can be understood as a "predetermined wavelength" in the sense of the foregoing, the propagation direction of the respective diffracted beam 76 or 80 differs by an angle $\Delta\theta$, as a result of the dispersion of the VPH 54. The angle $\Delta\theta$ is shown with respect to the first light component between the beams 72 and 76, and with respect to the second light component between the beams 60 and 80.

During diffraction, the first or second light component is diffracted away from the other light component, respectively. As a result of both light components being diffracted once at the VPH 54 and passing through the VPH 54 once, the angle between the light components, i.e. between the beams 76 and 82 in front of the detection unit 26 is equal to $2\Delta\theta$. In a respective manner, the angle between wavefronts 78 and 84 is equal to $2\Delta\theta$.

By passing the object light 46 twice through the VPH 54, in which a respective light component is transmitted and diffracted, a high spectral resolution can be achieved in this way. In addition, the transmissive diffraction element 22 bonded with the reflection bodies 24 configured as roof prisms 62 permits a very compact design of the spectroscopy apparatus 10. For example, the edge length, i.e., the sub-aperture of a respective roof prism 62 is approximately 1 mm. In the present case, the height of the spectroscopy module of VPH 54 and roof prisms 62 is approximately 11 mm, since there are a total of eleven roof prisms 62.

It is understood that the number of reflection bodies 24 and particularly roof prisms 62 could vary. For example, only one reflection body 24 and more specifically only one roof prism 62 could be provided within the scope of the invention.

FIG. 1 schematically illustrates with a dashed line 85 this latter case, in which only one reflection body 24 is present. Its apertures on the incident side and on the outgoing side preferably correspond to the sum of the apertures on the incident side and on the outgoing side of the respective reflection bodies 24, respectively, if several of them are used. If the counter body 68 is used as shown in FIG. 1, it comprises together with the one reflection body 24 the shape of a beam splitter cube, wherein the VPH 54 forms the "beam splitter layer".

The wavefronts 78 and 84 interfere at the detection unit 26, i.e. a self-interference of the object light 46 takes place. The corresponding interference pattern, for example fringes, is detected by the detection unit 26. The evaluation unit 28 can determine the respective wavelength $\lambda_R + \Delta\lambda$ based on a signal from the detection unit 26.

It is understood that in this way a plurality of wavelengths of the object light 46 can be determined via the spectroscopy apparatus 10. The evaluation of the signals of the detection unit 26 takes place at the evaluation unit 28 by means of Fourier transform methods.

During the evaluation, methods of interference technology known to the skilled person may optionally be preferred to the Fourier transform methods, for example methods of aberration correction.

The use of a plurality of reflection bodies 24 and sub-apertures 70 based thereon is shown to be advantageous for the quality of the interference pattern during self-interference. For this purpose, it is advantageous to use sufficiently small sub-apertures 70. With these, the respective interference patterns form better than with a large (sub-) aperture, because the lateral offset between the self-interfering beams can be kept small with a sufficiently small (sub-) aperture. The improved interference pattern as a result of the sub-apertures 70 results in the advantage of a high signal strength over the entire detection aperture 41, and the signal contributions of the individual sub-apertures 70 can be added together.

The spectroscopy apparatus 10 may comprise optical manipulation elements 90, optionally within a respective sub-aperture 70. The manipulation elements 90 are shown only in FIG. 1, using a roof prism 62 as an example.

The manipulation elements 90 are, for example, phase masks or amplitude masks. In the present arrangement, one manipulation element 90 is arranged between the VPH 54 and the roof prism 62, and another manipulation element 90 is arranged at the reflection element 52.

The manipulation elements 90 are, for example, sub-aperture dependent and differ from each other for different sub-apertures 70.

For example, beam shaping may be performed via the manipulation elements 90 to facilitate addition of the signal contributions from the sub-apertures 70.

Due to the dispersion of the VPH 54, the larger the offset wavelength $\Delta\lambda$ with respect to the base wavelength $\lambda_R$, the larger the angle is between the wavefronts 78, 84 of the first and second light components. However, regardless of the magnitude of the offset wavelength $\Delta\lambda$, the angle between the wavefronts 78, 84 is respectively $2\Delta\theta$, wherein the angle $\Delta\theta$ is between the beam 80 and the beam 60 when diffracted to the respective first order, and between the beam 76 and the beam 72, also when diffracted to the respective first order.

Figure 3A:
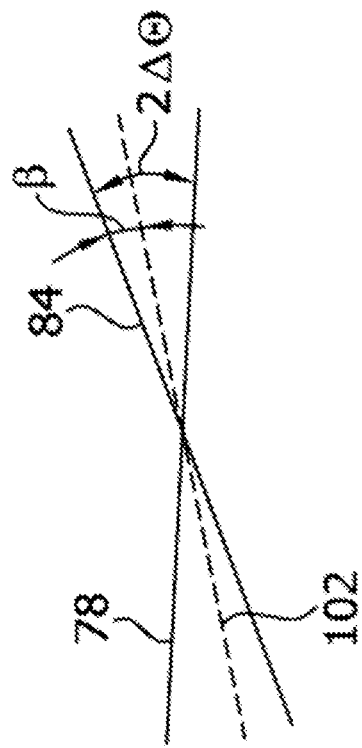
FIG. 3A: schematic representation of the relative position of two wavefronts when using the spectroscopy apparatus according to FIG. 1.
Figure 4A:
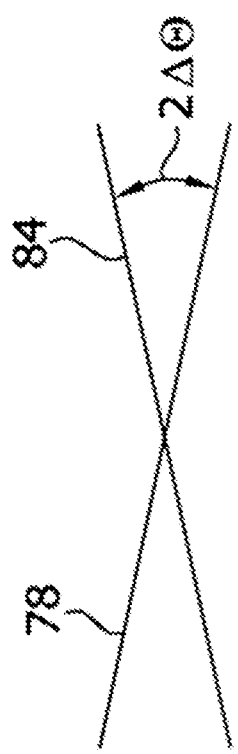
FIGS. 4A and 4B: representations respective to FIGS. 3A and 3B, wherein the angle between the wavefronts is different.

FIGS. 3A and 4A illustrate this as an example for two different offset wavelengths $\Delta\lambda$. Here, the offset wavelength $\Delta\lambda$ is smaller in FIG. 3A than in FIG. 4A, which is why the double angular offset $2\Delta\theta$ between the wavefronts 78 and 84 is smaller in FIG. 3A than in FIG. 4A.

It will be discussed below that the scatter spot 36 is spatially extended. This may cause a portion of the object light 46 to be incident at an angle $\beta$ with respect to the direction of arrival 56, i.e., the respective directions of arrival are inclined with respect to each other by the angle $\beta$ (FIG. 2). This portion of the object light, symbolized by beam 92, comprises a wavefront 94 which is also inclined by the angle $\beta$ with respect to the wavefront 40 incident in the direction of arrival 56.

If the base wavelength is present, then the wavefront 96 in upstream of the detection unit 26 also assumes an angle $\beta$ with respect to the wavefront 74 of the portion of the object light 46 incident in the direction of arrival 56. FIG. 2 shows here only for reasons of clarity the beams 98 before or 100 after reflection at the reflection element 52.

With respect to signal contributions lying outside the geometric focus at the scatter spot 36, the angle $\beta$ thus matches between the wavefronts 40 and 94 on the input side of the spectroscopy apparatus 10 as well as between the wavefronts 74 and 96 in front of the detection unit 26.

In a practical implementation, such angles $\beta$ can be easily implemented for common VPHs with a thickness of, for example, less than 100 µm, if, for example, the focal length of the converging lens 18 is in the region of about 100 mm and the radius of the scatter spot 36 is in the region of about 0.5 mm.

Correspondingly, the same applies to the other wavelengths $\lambda_R + \Delta\lambda$ im Raman spectrum also at different offset wavelengths, wherein the $2\Delta\theta$-tilt between the wavefronts must also be taken into account.

Figure 3B:
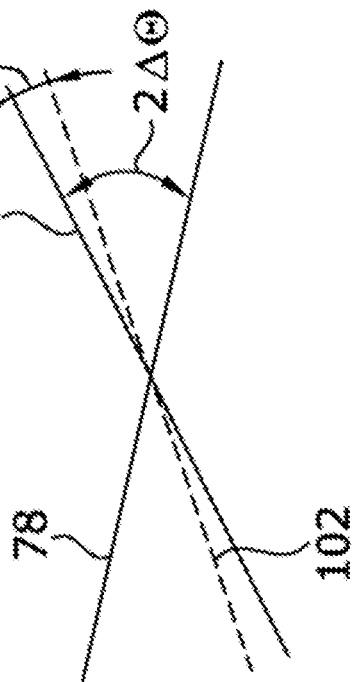
FIG. 3B: a representation respective to FIG. 3A, wherein the wavefronts are tilted by an angle.
Figure 4B:
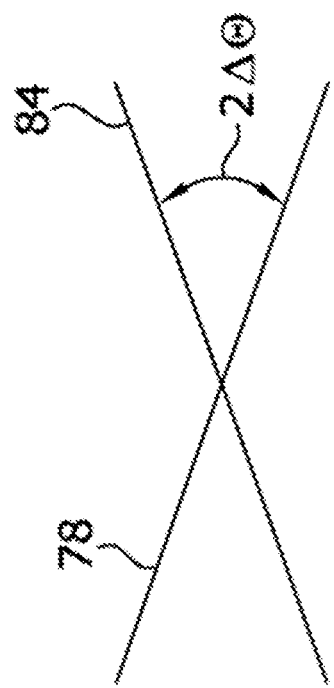

This is shown schematically in FIGS. 3B and 4B. The wavefronts 78, 84 in front of the detection unit 26 are tilted relative to each other by the angle $2\Delta\theta$, but with respect to the situation according to FIG. 3A (marked by a dashed line 102) they are tilted together by the angle $\beta$.

The situation according to FIG. 4B behaves accordingly in relation to FIG. 4A, wherein, however, the offset wavelength $\Delta\lambda$ is greater than in the situation according to FIGS. 3A and 3B.

Accordingly, the angle $2\Delta\theta$ between the wavefronts 78 and 84 at the offset wavelengths $\Delta\lambda$ is independent of whether the object light 46 is incident in the defined direction of arrival 56 or in the different direction of arrival inclined at an angle $\beta$ thereto. For this reason, the spectroscopy apparatus 10 comprises a high acceptance angle. Regardless of the "origin" of the object light 46, or a portion thereof, from the scatter spot 36, a matching spectrum can be obtained because the interference patterns add up in phase for each angle $\beta$. Thus, a high sensitivity of the spectroscopy apparatus can be obtained.

In a practical implementation, a scatter spot 36 of max. approx. 10 mm diameter can be spectroscoped at an acceptance angle of, for example, about 5° and a focal length of about 50 mm.

In the spectroscopy apparatus 10 explained so far, it is provided that the roof prisms 62 are symmetrically constructed, wherein the sides 64, 65 are of equal length (length 104 in FIG. 2). Thus, the respective light path for the first light component and the second light component from the diffraction element 22 to the respective reflection element 50, 52 (and back) is of equal length, wherein light beams extending centrally or essentially centrally within the sub-aperture are assumed.

As explained preceding, it may be advantageous if the light paths of the first light component and the second light component are of different lengths. This could be achieved, for example, by an asymmetrical configuration of the reflection body 24, in particular a roof prism 62. For example, the two sides 64, 65 are of different lengths.

FIG. 6 shows an exemplary schematic representation of a reflection body 24, configured as an inverted prism and in particular as a roof prism 62, to achieve the same effect of light paths of different lengths.

The roof prism 62 is isosceles-rectangular in shape, wherein the sides 64, 65 are of equal length and comprise the length 104, respectively. The length 104 is composed of a length 106 and a length 108. With respect to the first light component, a manipulation element 90 is arranged on the roof prism 62, in this case in the form of an amplitude mask. The manipulation element 90 acts as a blocking element or shading element with respect to the first light component. The first and second light components are shown here using the example of beams 58, 60 of the base wavelength.

In another aspect, the roof prism 62 comprises a respective side length 106. On one side, along the side 64, further material of length 108 is integrally attached, which is blocked or shaded at the diffraction element facing over the manipulation element 90.

The roof prism 62 acts as an asymmetric prism. With respect to the centered or essentially centered incident first and second light components, light paths of different lengths result.

It is understood that the difference in path length between the light components could alternatively be achieved by positioning the manipulation element 90 in a different manner.

Roof prisms 62 as shown in FIG. 6 can be used in the spectroscopy apparatus according to the invention. This offers, for example, the possibility of differential Raman spectroscopy, which has already been explained in the preceding.

Here, the wavelength of the excitation light 34 can be varied. For a length 108 of 200 μm, for example, a wavelength difference of approximately 0.5 nm to 0.6 nm at an excitation wavelength of 670 nm proves suitable, wherein these specifications are only exemplary and serve the purpose of explanation.

The path length difference results in a phase difference of the interference patterns of approximately 180° (Pi) due to the different excitation wavelengths. The evaluation unit 28, which is synchronized with the illumination unit 32, can subtract the spectra determined during the respective measurement from each other.

During the subtraction, contributions from incoherent and/or broadband radiation that remain essentially unchanged by the shift in excitation wavelength and originate, for example, from fluorescence can be largely reduced or ideally eliminated in this way.

REFERENCE SIGN LIST

10 Spectroscopy apparatus
12 Examination object
14 Illumination unit
16 Focusing lens
18 Convex lens
20 Blocking element
22 Diffraction element
24 Reflection body
26 Detection unit
28 Evaluation unit
30 Casing
32 Light source
34 Excitation light
36 Scatter spot
38 Input aperture
40 Wavefront
41 Detection aperture
42 VPH
44 Coordinate system
45 Extension
46 Object light
48 Arrow
50 First reflection element
52 Second reflection element
54 VPH
56 Direction of arrival
58, 60 Beam
62 Roof prism
64, 65 Side
66 Counter prism
68 Counter body
70 Sub-aperture
72, 76 Beam
74, 78 Wavefront
80, 82 Beam
84 Wavefront
85 Dashed line
90 Manipulation element
94, 96 Wavefront
92, 98, 100 Beam
102 Dashed line
104, 106, 108 Length

The invention claimed is:

1. An optical spectroscopy apparatus comprising a transmissive diffraction element (22) onto which object light (46) emanating from an examination object (12) is incident via an input aperture (38) of the spectroscopy apparatus (10), a first reflection element (50) and a second reflection element (52) which are arranged downstream of the transmissive diffraction element (22) with respect to a defined direction of arrival (56) of the object light (46), and a detection unit (26), which is arranged downstream of the transmissive diffraction element (22) with respect to object light (46) reflected by the reflection elements (50, 52), and an evaluation unit (28) coupled to the detection unit (26), wherein the transmissive diffraction element forms a beam splitter element, wherein a first light component of the object light (46) is transmitted by the transmissive diffraction element (22), is reflected at the first reflection element (50) and is diffracted at the transmissive diffraction element (22) in a wavelength-dependent manner in a direction of the detection unit (26), wherein a second light component of the object light (46) is diffracted at the transmissive diffraction element (22) in a wavelength-dependent manner in a direction of the second reflection element (52), is reflected therefrom in the direction of the detection unit (26), and is transmitted by the transmissive diffraction element (22), wherein wavefronts (74, 78, 84) of the first light component and of the second light component interfere at the detection unit (26) depending on the wavelength of the object light (46) to form a respective interference pattern, on the basis of which at least one wavelength of the object light (46) can be determined by the evaluation unit (28), wherein an angle ($2\Delta\theta$) between the wavefronts (74, 78, 84) of the first light component and the second light component is twice as large as an angle ($\Delta\theta$) between a first-order diffraction direction for the first or the second light component at a predetermined wavelength and the first-order diffraction direction for the wavelength deviating therefrom.

2. The spectroscopy apparatus according to claim 1, wherein due to a dispersion of the transmissive diffraction element (22), the wavefronts (74, 78, 84) of the first light component and the second light component enclose an angle (Δθ) between them which is dependent on the wavelength of the object light (46) and is greater the greater the deviation of the wavelength from the predetermined wavelength.

3. The spectroscopy apparatus according to claim 1, wherein the spectroscopy apparatus (10) is free of moving mechanical elements.

4. The spectroscopy apparatus according to claim 1, wherein the transmissive diffraction element (22) is a spectral grating formed as a phase grating.

5. The spectroscopy apparatus according to claim 1, wherein the transmissive diffraction element (22) is positioned in Littrow arrangement relative to the defined direction of arrival (56) with respect to a predetermined wavelength at which an angle of incidence of the object light on the transmissive diffraction element (22) corresponds to a diffraction angle of the second light component to a first order.

6. The spectroscopy apparatus according to claim 1, wherein the transmissive diffraction element (22) is formed in such a way that, with respect to a predetermined wavelength, 50% of the object light is transmitted as a first light component or diffracted as a second light component, respectively.

7. The spectroscopy apparatus according to claim 1, wherein the wavefronts (74, 78, 84) of the first light component and the second light component enclose an angle (2β) between them which is independent of whether the object light is incident in the defined direction of arrival (56) or is in a different direction of arrival inclined relative thereto by an angle (β).

8. The spectroscopy apparatus according to claim 1, wherein the first reflection element (50) and the second reflection element (52) are two adjacent sides of at least one reflection body (24) that enclose an angle.

9. The spectroscopy apparatus according to claim 8, wherein the at least one reflecting body (24) is arranged adjacent or with interposition of an optical manipulation element (90) adjacent to the transmissive diffraction element (22).

10. The spectroscopy apparatus according to claim 1, wherein the first light component passes from the transmissive diffraction element (22) to the first reflection element (50, 52) and back along a light path to the transmissive diffraction element (22), and wherein the second light component passes from the transmissive diffraction element (22) to the second reflection element (52) and back along a light path to the transmissive diffraction element (22), wherein the light paths of the first and the second light component are of equal length or of different lengths.

11. The spectroscopy apparatus according to claim 10, wherein the Spectroscopy apparatus (10) is configured to successively emit light with two excitation wavelengths different from one another via an illumination unit (14), wherein as a result of the light paths of different lengths a phase difference of the interference patterns occurring in each case can be achieved with respect to one another.

12. The spectroscopy apparatus according to claim 1, wherein the spectroscopy apparatus (10) comprises or forms a plurality of sub-apertures (70), wherein the object light (46) incident on the transmissive diffraction element (22) is split within a respective sub-aperture (70) into a first light component and a second light component and reflected at respective first reflection elements (50) or second reflection elements (52).

13. The spectroscopy apparatus according to claim 12, wherein within each sub-aperture (70) the spectral information about the at least one wavelength of the object light is contained in the wavefronts of the first light component and the second light component originating from this sub-aperture (70).

14. The spectroscopy apparatus according to claim 12, wherein a plurality of reflection bodies (24) arranged side by side in the direction of extension of the transmissive diffraction element (22) and having a respective first reflection element (50) and a respective second reflection element (52) are provided, which reflection bodies (24) define a respective sub-aperture (70).

15. The spectroscopy apparatus according to claim 12, wherein the spectroscopy apparatus (10) comprises at least one optical manipulation element (90) associated with a respective sub-aperture (70).

16. The spectroscopy apparatus according to claim 15, wherein light paths of different lengths of the first light component and the second light component from the transmissive diffraction element (22) to the respective reflection element (50, 52) and back can be achieved by means of at least one manipulation element (90) on a reflection body (24).

17. The spectroscopy apparatus according to claim 1, wherein the spectroscopy apparatus (10) comprises an illumination unit (14) which comprises at least one light source (32) for illuminating the examination object (12).

18. The spectroscopy apparatus according to claim 1, wherein the spectroscopy apparatus (10) comprises at least one of the following upstream of the transmissive diffraction element (22) with respect to the direction of arrival (56):
  a convex lens (18) or concave mirror for collecting object light (46) emanating from the examination object (12);
  at least one blocking element (20) for filtering or reflecting object light (46) outside a predetermined spectral region.

19. An optical spectroscopy apparatus comprising:
  a transmissive diffraction element (22) onto which object light (46) emanating from an examination object (12) is incident via an input aperture (38) of the spectroscopy apparatus (10),
  a first reflection element (50) and a second reflection element (52) which are arranged downstream of the transmissive diffraction element (22) with respect to a defined direction of arrival (56) of the object light (46), and
  a detection unit (26), which is arranged downstream of the transmissive diffraction element (22) with respect to object light (46) reflected by the reflection elements (50, 52),
  and an evaluation unit (28) coupled to the detection unit (26),
  wherein the transmissive diffraction element forms a beam splitter element,
  wherein a first light component of the object light (46) is transmitted by the transmissive diffraction element (22), is reflected at the first reflection element (50) and is diffracted at the transmissive diffraction element (22) in a wavelength-dependent manner in the direction of the detection unit (26),
  wherein a second light component of the object light (46) is diffracted at the transmissive diffraction element (22) in a wavelength-dependent manner in the direction of the second reflection element (52), is reflected therefrom in the direction of the detection unit (26), and is transmitted by the transmissive diffraction element (22), wherein wavefronts (74, 78, 84) of the first light component and of the second light component interfere at the detection unit (26) depending on the wavelength of the object light (46) to form a respective interference pattern, on the basis of which at least one wavelength of the object light (46) can be determined by the evaluation unit (28), wherein the wavefronts (74, 78, 84) of the first light component and the second light component enclose an angle (2) between them which is independent of whether the object light is incident in the defined direction of arrival (56) or is in a different direction of arrival inclined relative thereto by an angle ($\beta$).

* * * * *